United States Patent [19]

Bandurco et al.

[11] Patent Number: 4,634,769

[45] Date of Patent: Jan. 6, 1987

[54] PROCESS FOR THE PREPARATION OF 8-HALO-5,6-DIALKOXYQUINAZOLINE-2,4-DIONES AND THEIR SALTS

[75] Inventors: Victor T. Bandurco, Bridgewater; Robert A. Mallory, Somerville; Jeffrey B. Press, Rocky Hill; Harvey M. Werblood, Bridgewater, all of N.J.

[73] Assignee: Ortho Pharmaceutical Corporation, Raritan, N.J.

[21] Appl. No.: 654,350

[22] Filed: Sep. 25, 1984

[51] Int. Cl.$^4$ .......................................... C07D 239/80
[52] U.S. Cl. ............................ 544/285; 560/29; 560/46; 560/55; 562/434
[58] Field of Search ........................................ 544/285

[56] References Cited

U.S. PATENT DOCUMENTS

| | | | |
|---|---|---|---|
| 3,983,120 | 9/1976 | Beverung et al. | 544/286 |
| 3,988,340 | 10/1976 | Partyka et al. | 544/286 |
| 4,146,717 | 3/1979 | Yamamoto et al. | 546/286 |
| 4,202,895 | 5/1980 | Yamamoto et al. | 546/286 |

OTHER PUBLICATIONS

Lucas, *Organic Chemistry*, Sec. Ed., 1953, American Book Co., New York, pp. 211–213, 351–353, 460–462, 464.

Brown, Fused Pyrimidines, Part I, 1967, Interscience Publishers, New York, pp. 120–122.

Primary Examiner—Glennon H. Hollrah
Assistant Examiner—James H. Turnipseed
Attorney, Agent, or Firm—Benjamin F. Lambert

[57] ABSTRACT

A process for the preparation of 8-halo-5,6-dialkoxyquinazoline-2,4-diones and their metal salts is described. The diones are active cardiotonic agents.

7 Claims, No Drawings

PROCESS FOR THE PREPARATION OF 8-HALO-5,6-DIALKOXYQUINAZOLINE-2,4-DIONES AND THEIR SALTS

The present invention relates to a method of preparing 8-halo-5,6-dialkoxyquinazoline-2,4-diones and their metal salts. The diones and their salts are active cardiotonic agents.

The 5,6-dialkoxyquinazoline-2,4-diones which are the subject of this invention have the following formula:

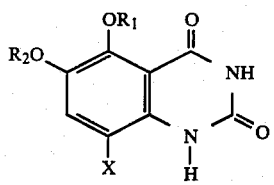

wherein $R_1$ and $R_2$ are the same or different lower alkyl having 1-4 carbon atoms and X is chloro or bromo.

The preparation of the diones and their salts is illustrated by the following schematic diagram:

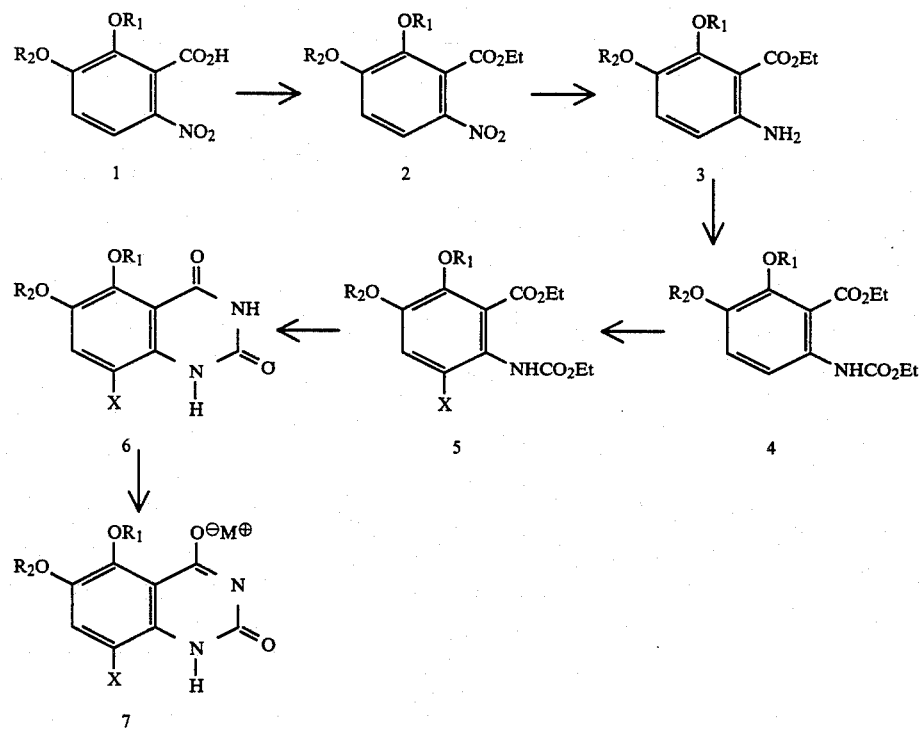

wherein $R_1$ and $R_2$ are the same or different lower alkyl, $M^+$ is sodium or potassium and X is chloro or bromo.

In each of the steps in the process, the products are isolated where indicated and characterized by techniques known to those skilled in the art.

As can be seen from the above diagram, the first step in the synthesis of the 8-halo-5,6-dialkoxyquinazoline-2,4-diones involves the esterification of a 2,3-dialkoxy-6-nitrobenzoic acid compound (1). The esterification step is carried out by reacting the nitrobenzoic acid compound (1) with an esterifying agent such as triethyl orthoformate or ethanolic hydrogen chloride. The reaction can be carried out at temperatures between room temperature and about 160° C. The preferred reaction temperature is the reflux temperature of the solvent. While no solvent is required, suitable solvents which can be employed include dimethylformamide, ethanol, toluene, xylene, diglyme, and the like. The nitrobenzoate is then converted to the corresponding amino ester (3) by reduction with a reducing agent such as hydrogen on palladium or platinum oxide catalyst or iron in acetic acid. The amino ester (3) is then converted to the dialkoxybenzenecarbamate (4) by reaction with an alkyl halo formate such as ethyl chloroformate or propyl chloroformate in a suitable solvent such as chloroform, methylene chloride, ether, tetrahydrofuran, dioxane, toluene, and the like. The reaction is carried out at room temperature and the dialkoxybenzenecarbamate (4) can be used in the next step without first isolating it from the reaction mixture. The halogen is introduced into the molecule (5) by reacting the benzenecarbamate with a halogenating agent such as sulfuryl chloride, chlorine, N-chlorosuccinimide, calcium hypochlorite, N-bromosuccinimide and the like. The halogenation reaction is carried out at room temperature in a suitable solvent such as chloroform, methylene chloride, pyridine, toluene, dichloroethane, and the like. The halo 3,4-dialkoxybenzenecarbamate (5) is then cyclized to the quinazoline-2,4-dione by reaction with ammonia or ammonium acetate. The reaction is preferably carried out at elevated temperatures 100°-170° C., preferably 125°-130° C.

The metal salts of the 8-halo-5,6-dialkoxyquinazolin-2,4-diones are prepared by treating the dione with strong base such as sodium or potassium hydroxide.

EXAMPLE 1

Ethyl 2,3-dimethoxy-6-nitrobenzoate (2)

2,3-Dimethoxy-6-nitrobenzoic acid (1, 180.0 g, 0.792 mole) was dissolved in triethyl orthoformate (466.2 g, 3.14 mole) optionally containing dimethylformamide (4 mL) and the mixture was heated to reflux for one hour. The solvent was removed in vacuo, the residue was extracted with chloroform (2 L) and the organic layer was dried over magnesium sulfate. Removal of the solvent in vacuo gave the product as a pale brown oil which crystallized upon standing at room temperature, 202 g (100%, m.p. 70°–72° C.). This material could be recrystallized from isopropanol but was generally reacted in the next step without additional purification.

EXAMPLE 2

Ethyl 6-amino-2,3-dimethoxybenzoate (3)

Ethyl 2,3-dimethoxy-6-nitrobenzoate (200 g, 0.979 mole) was dissolved in ethanol (2 L) containing 5% palladium on carbon and hydrogenated until the theoretical amount of hydrogen was absorbed. Filtration and removal of the solvent in vacuo provided the product as a yellow oil, 220.6 g (98.0%).

EXAMPLE 3

Ethyl 2-Carboethoxy-6-chloro-3,4-dimethoxybenzenecarbamate (5)

A. A solution of ethyl 6-amino-2,3-dimethoxybenzoate (30.0 g, 0.13 mole) and ethyl chloroformate (16.5 g, 0.16 mole) in chloroform (250 mL) was added to a solution of sodium bicarbonate (33.3 g, 0.40 mole) in water (100 mL) and the mixture was stirred gently at room temperature for 6 hours. The layers were separated and the chloroform solution was dried over sodium sulfate and filtered. This solution was used directly in the next reaction without further isolation and/or purification.

B. The chloroform solution of ethyl 2-carboethoxy-3,4-dimethoxybenzenecarbamate prepared in A above was treated with sulfuryl chloride (30.2 g, 0.22 mole) and optionally with sodium bicarbonate (33.3 g, 0.40 mole) and the mixture was stirred at room temperature for 4 hours. An additional charge of sodium bicarbonate (3.3 g, 0.04 mole) and sulfuryl chloride (3.0 g, 0.02 mole) was added and stirring was continued for 16 hours. Filtration and concentration of the filtrate provided crude product as an oil which was crystallized from aqueous methanol. The resultant solid was dissolved in chloroform and the solution was dried, filtered and concentrated to give an oil which was crystallized from hexanes; 37.3 g (85%), mp 111°–113° C.

EXAMPLE 4

8-Chloro-5,6-dimethoxyquinazolin-2,4-dione (6)

A mixture of ethyl 2-carboethoxy-6-chloro-3,4-dimethoxybenzenecarbamate (34.0 g, 0.102 mole), and ammonium acetate (183 g) was heated at 125°–130° C. for 16 hours. The mixture was then cooled to 90° C., water (110 mL) was added and cooling to 15° C. gave a precipitate which was collected by filtration. The crude product was washed with water (200 mL) and acetone (200 mL) and dried to give the product as a tan solid. Yield 24.3 g (92.4%) m.p. 288°–290° C. The brown solid was dissolved in hot acetic acid (400 mL), treated with charcoal (8 g), filtered and cooled to 15° C. The precipitate was collected by filtration, washed with acetone and dried to give the product as white crystals, mp 292°–294° C.

EXAMPLE 5

8-Chloro-5,6-dimethoxyquinoxazolin-2,4-dione Mono Sodium Salt (7)

8-Chloro-5,6-dimethoxyquinoxazolin-2,4-dione (5.3 g, 0.021 mole) was dissolved in 5% aqueous sodium hydroxide (23 mL). After stirring for 10 minutes the reaction mixture was filtered and the collected solid was washed thoroughly with methanol, ethanol, acetone and finally petroleum ether. The dried solid (5.0 g, 87.7%) melted with decomposition at 320° C.

Preparation of 2,3-dimethoxy-6-nitrobenzoic acid

EXAMPLE A

2-Hydroxy-3-methoxybenzaldehyde benzenesulfonate

A solution of o-vanillin (537.5 g, 3.54 mole) in water (3.6 L) containing potassium hydroxide (215 g, 3.77 mole) was treated with benzenesulfonyl chloride (360 mL, 2.83 mole) dropwise over a period of one hour. Methylene chloride (75 ml) was added and the mixture was stirred overnight. The resultant solid was collected by filtration and washed with 500 mL of 5% aqueous potassium hydroxide and 1 L of water. The solid was dried in vacuo at 70°–90° C. to give the title compound, 750 g, mp 115°–119° C.

EXAMPLE B

2-Hydroxy-3-methoxy-6-nitrobenzaldehyde benzenesulfonate

2-Hydroxy-3-methoxybenzaldehyde benzenesulfonate (200 g, 0.685 mole) was added to 90% nitric acid (400 mL) with the temperature maintained at 0°±2° over a period of one-half to one hour. The reaction mixture was stirred an additional 0.5 hour and poured over ice (2.5 L) with stirring. After standing several hours, the solid was collected by filtration and washed with water (500 mL). The solid was then suspended in acetone (1.25 L) and the mixture was heated to reflux for 0.5 hour, concentrated to 500 mL and cooled to 15° C. The resultant solid was collected by filtration and washed with cold acetone (125 mL) to provide the title compound, 138.5 g (60%), mp 151°–155° C.

EXAMPLE C

2-Hydroxy-3-methoxy-6-nitrobenzaldehyde potassium salt

2-Hydroxy-3-methoxy-6-nitrobenzaldehyde benzenesulfonate (80.0 g, 0.237 mole) was slurried in methanol (4.0 L) and heated to reflux. Aqueous potassium hydroxide (51.2 g in 110 mL) was added with stirring to the refluxing solution over 0.5 hour and heating was continued an additional 0.5 hour. The thick paste which formed was cooled to room temperature and filtered to give the product as a vermillion solid, 52.8 g (95%). This material was not further purified but carried on to the next step.

EXAMPLE D 2,3-Dimethoxy-6-nitrobenzaldehyde

2-Hydroxy-3-methoxy-6-nitrobenzaldehyde potassium salt was slurried in acetone (500 mL) containing potassium carbonate (50 g) and the suspension was treated with dimethylsulfate (18.5 mL) and heated to reflux for one hour. An additional aliquot (18.5 mL) of dimethylsulfate was then added and the mixture was heated overnight. After 24 hours the red color of the potassium salt was virtually absent. The salts were removed by filtration, the filtrate was concentrated and the residue was recrystallized from isopropanol to give the title compound 40.0 g (80% from 3) mp 109°–110° C.

EXAMPLE E

2,3-Dimethoxy-6-nitrobenzoic acid 2,3-Dimethoxy-6-nitrobenzaldehyde (40.0 g, 0.19 mole) was treated with acetone (275 mL) and warmed to 50° C. A solution of potassium permanganate in water (60 g/L) was added slowly at 50°–70° C. over a period of 16–20 hours until thin layer chromatographic analysis revealed complete absence of the starting material. Isopropanol (7.5 mL) was then added and the mixture was heated an additional hour. The precipitated manganese dioxide was removed by filtration and the filter cake was washed with 3% aqueous potassium hydroxide (ca 175–200 mL). The combined filtrates were acidified with hydrochloric acid and the precipitate was collected by filtration and dried in vacuo. The crude product was recrystallized from acetone to give the pure material, 28.3 g (67%), mp 187°–189° C.).

We claim:

1. The process for the preparation of a compound of the formula

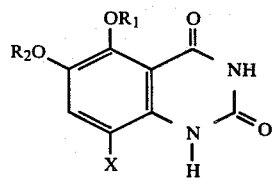

which comprises reacting a compound of the formula

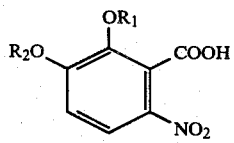

with an esterifying agent to form a nitro ester of the formula

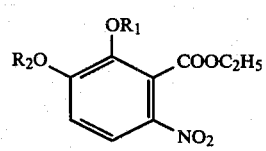

reacting the nitro ester with a reducing agent to form an amino ester of the formula

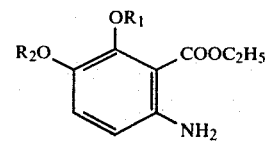

reacting the amino ester first with an alkyl chloroformate to form a benzenecarbamate and reacting the benzenecarbamate with a halogenating agent to form a halogenated benzenecarbamate of the formula

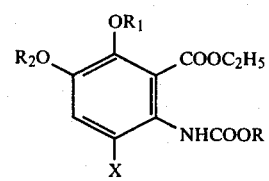

and reacting the halogenated benzenecarbamate with a cyclizing agent wherein X is chloro or bromo and R, $R_1$ and $R_2$ are the same or different lower alkyl.

2. The process of claim 1 wherein the reducing agent is hydrogen, the esterifying agent is triethylorthoformate and the alkyl chloroformate is ethyl chloroformate.

3. The process of claim 1 wherein the halogenating agent is sulfuryl chloride and the cyclizing agent is ammonia.

4. The process for the preparation of a compound of the formula

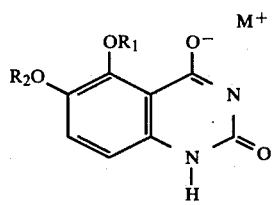

which comprises reacting a compound of the formula

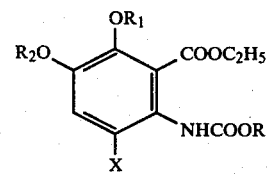

with a cyclizing agent to form a dione of the formula

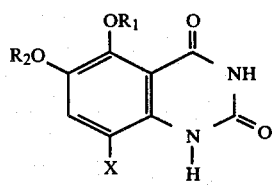

and treating the dione with an alkali metal hydroxide wherein R, $R_1$ and $R_2$ are the same or different lower alkyl, X is halo and $M^+$ is sodium or potassium.

5. The process of claim 4 wherein the alkali metal hydroxide is sodium hydroxide.

6. The process of claim 4 wherein the cyclizing agent is ammonia.

7. The process of claim 4 wherein X is chloro.

* * * * *